United States Patent
Kanan et al.

(10) Patent No.: US 12,358,882 B2
(45) Date of Patent: Jul. 15, 2025

(54) CARBONATE-PROMOTED CARBOXYLATION AT HIGH RATES

(71) Applicant: The Board of Trustees of the Leland Stanford Junior University, Stanford, CA (US)

(72) Inventors: Matthew W. Kanan, Palo Alto, CA (US); Aanindeeta Banerjee, Oakland, CA (US); Amy Delano Frankhouser, Oakland, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 611 days.

(21) Appl. No.: 17/793,890

(22) PCT Filed: Feb. 5, 2021

(86) PCT No.: PCT/US2021/016772
§ 371 (c)(1),
(2) Date: Jul. 19, 2022

(87) PCT Pub. No.: WO2021/158890
PCT Pub. Date: Aug. 12, 2021

(65) Prior Publication Data
US 2023/0048043 A1    Feb. 16, 2023

Related U.S. Application Data

(60) Provisional application No. 62/970,969, filed on Feb. 6, 2020.

(51) Int. Cl.
*C07D 307/68* (2006.01)

(52) U.S. Cl.
CPC .................. *C07D 307/68* (2013.01)

(58) Field of Classification Search
CPC .............................. C07D 307/68; C07C 51/02
See application file for complete search history.

(56) References Cited

U.S. PATENT DOCUMENTS

| 4,508,920 | A | 5/1985 | Stopp et al. |
| 9,000,245 | B2 | 4/2015 | O'Connor et al. |
| 10,160,740 | B2 * | 12/2018 | Kanan .............. C07C 51/15 |
| 10,710,971 | B2 * | 7/2020 | Kanan .............. C07C 51/02 |
| 2019/0084953 | A1 | 3/2019 | Kanan et al. |

FOREIGN PATENT DOCUMENTS

WO      2016/153937      9/2016

OTHER PUBLICATIONS

Extended European Search Report and Search Opinion for European Application No. 21751291 dated Feb. 28, 2024.
Dick et al. "A Scalable Carboxylation Route to Furan-2,5-dicarboxylic Avid" Green Chem., 2017, vol. 19, pp. 2966-2972.
International Search Report from International Application No. PCT/US21/16772 dated Apr. 15, 2021.
Written Opinion from International Application No. PCT/US21/16772 dated Apr. 15, 2021.
Aanindeeta Banerjee et al. "Carbon dioxide utilization via carbonate-promoted C—H carboxylation" Nature., Mar. 2016, vol. 531, No. 7593, pp. 215-219.
Supplementary Partial European Search Report and Provisional Opinion Accompanying the Partial Search Result for European Application No. 21751291 dated Dec. 14, 2023.

* cited by examiner

*Primary Examiner* — Kamal A Saeed
(74) *Attorney, Agent, or Firm* — Beyer Law Group LLP (57) ABSTRACT

A method for synthesizing furan-2, 5-dicarboxylate ($FDCA^{2-}$) is provided. Furan-2-carboxylate is provided with an inorganic base in the form of an inorganic base salt, wherein the furan-2-carboxylate and the inorganic base salt form a mixture. A $CO_2$ gas is provided to the mixture. The mixture is heated to a temperature to at least partially melt the mixture, wherein the heating of the mixture causes the synthesizing of a $M_xFDCA$ solid, wherein $M_xFDCA$ denotes a salt comprising furan-2,5-dicarboxylate ($FDCA^{2-}$) and cation $M^+$ and/or $M^{2+}$, where x is a number between 1 and 2, inclusive. The mixture containing furan-2-carboxylate is mechanically agitated, wherein the mechanically agitating breaks up the $M_xFDCA$ solid.

20 Claims, 6 Drawing Sheets

CARBONATE-PROMOTED CARBOXYLATION AT HIGH RATES

CROSS REFERENCE TO RELATED APPLICATIONS

This application claims priority under 35 U.S.C. § 119 from U.S. Application No. 62/970,969, filed Feb. 6, 2020, entitled PROCESS DESIGN FOR CARBONATE-PROMOTED CARBOXYLATION AT HIGH RATES by Kanan et al., which is incorporated herein by reference for all purposes.

GOVERNMENT RIGHTS

This invention was made with Government support under contract DE-AR0000961 awarded by the U.S. Department of Energy. The Government has certain rights in the invention.

BACKGROUND

This disclosure relates to the synthesis of furan-2,5-dicarboxylate ($FDCA^{2-}$) and furan-2,5-dicarboxylic acid (FDCA) from $CO_2$ and furan-2-carboxylic acid and/or furan-2-carboxylate.

SUMMARY

In accordance with this disclosure, a method for synthesizing furan-2, 5-dicarboxylate ($FDCA^{2-}$) is provided. Furan-2-carboxylate is provided with an inorganic base in the form of an inorganic base salt, wherein the furan-2-carboxylate and the inorganic base salt form a mixture. A $CO_2$ gas is provided to the mixture. The mixture is heated to a temperature to at least partially melt the mixture, wherein the heating of the mixture causes the synthesizing of a $M_xFDCA$ solid, wherein $M_xFDCA$ denotes a salt comprising furan-2,5-dicarboxylate ($FDCA^{2-}$) and cation $M^+$ and/or $M^{2+}$, where x is a number between 1 and 2, inclusive. The mixture containing furan-2-carboxylate is mechanically agitated, wherein the mechanically agitating breaks up the $M_xFDCA$ solid.

In another manifestation, a method for synthesizing furan-2, 5-dicarboxylate ($FDCA^{2-}$) is provided. Furan-2-carboxylate is provided with an inorganic base in the form of an inorganic base salt, wherein the furan-2-carboxylate and the inorganic base salt form a mixture. A $CO_2$ gas is provided to the mixture. The mixture is heated to a temperature to at least partially melt the mixture, wherein the heating of the mixture causes the synthesizing of a $M_xFDCA$ solid, wherein $M_xFDCA$ denotes a salt comprising furan-2,5-dicarboxylate ($FDCA^{2-}$) and cation $M^+$ and/or $M^{2+}$, where x is a number between 1 and 2, inclusive. The mixture is cooled to solidify the mixture to form a solid mixture. Particle sizes of the solid mixture are reduced. The mixture is reheated while providing a $CO_2$ gas to partially melt the mixture.

The invention and objects and features thereof will be more readily apparent from the following detailed description and appended claims when taken with the drawings.

BRIEF DESCRIPTION OF THE DRAWINGS

The present disclosure is illustrated by way of example, and not by way of limitation, in the figures of the accompanying drawings and in which like reference numerals refer to similar elements and in which.

DETAILED DESCRIPTION OF ILLUSTRATED EMBODIMENTS

Furan-2,5-dicarboxylic acid (FDCA) is a bio-based molecule that can be used to make performance-advantaged polymers and chemicals with wide ranging applications. In particular, polyesters made from FDCA have attracted substantial commercial interest because they have superior gas barrier, thermal, and mechanical properties compared to the commonly used polyester polyethylene terephthalate (PET) (Burgess, et al. *Macromolecules,* 47, 1383-1391 (2014)), a commodity polymer produced on a scale of many megatons per year. Several processes have been developed to synthesize FDCA starting from glucose or fructose. While these feedstocks are widely available from the food ingredient industry, the production of FDCA from glucose or fructose faces a number of technical difficulties including a challenging oxidation step involving three substrate oxidations, the use of organic solvents that require complicated recycle loops and lead to side products, and laborious purifications to separate FDCA from a monoaldehyde impurity that compromises its use in polymer applications. In addition, the use of food ingredients as feedstocks for a chemical with high-volume applications is undesirable from a sustainability perspective because of the environmental footprint of agriculture and the potential for incentivizing detrimental land use changes.

As an alternative to processes starting from glucose or fructose, FDCA can be produced from furfural and $CO_2$ by a process comprising: i) oxidation of furfural to furan-2-carboxylic acid/furan-2-carboxylate; ii) carbonate-promoted C—H carboxylation of furan-2-carboxylate to produce furan-2,5-dicarboxylate, described in U.S. Pat. No. 10,160,740 entitled, "CARBONATE-PROMOTED CARBOXYLATION REACTIONS FOR THE SYNTHESIS OF VALUABLE ORGANIC COMPOUNDS", by Kanan et al, which is incorporated by reference for all purposes, iii) protonation of furan-2,5-dicarboxylate to produce FDCA. This approach has a number of advantages including i) it requires only a single substrate oxidation (furfural to furan-2-carboxylic acid/furan-2-carboxylate); ii) it avoids the formation of the problematic monoaldehyde impurity; iii) it does not require the use of organic solvents; iv) the feedstock furfural has been produced industrially from lignocellulose (inedible biomass) on a large scale for many decades, as described in Lange et al. *Chem Sus Chem* 5, 150-166 (2012), which is incorporated b reference for all purposes.

Carbonate-promoted C—H carboxylation of furan-2-carboxylate described herein has major advantages over other methods to produce furan-2,5-dicarboxylate from furan-2-carboxylic acid, furan-2-carboxylate, or their derivatives. Furan-2-carboxylic acid has previously been converted into furan-2,5-dicarboxylate by reacting with two equivalents of lithium diisopropylamide (LDA) followed by $CO_2$ in an aprotic organic solvent, which is described in Thiyagarajan et al. *RSC Adv.* 3, 15678-15686 (2013), which is incorporated by reference for all purposes. LDA is pyrophoric, energy intensive, and much more expensive than any monomer for high-volume plastic.

A method to carboxylate methyl furan-2-carboxylate to form 5-(methoxycarbonyl)furan-2-carboxylate using a photoredox catalysis with $Cs_2CO_3$ as the base has been reported in Schmalzbauer et al. *Chem*, 6, 2658-2672, (2020), which is incorporated by reference for all purposes. Although the reaction proceeds under mild conditions, it has a number of limitations including i) it requires high loading (20 mol %) of an organic photocatalyst that requires multiple steps to synthesize; ii) it uses 3 equivalents of $Cs_2CO_3$; iii) it requires intense light applied over a long reaction time.

Methods have also been described to convert aromatic mono-carboxylates into dicarboxylates using disproportionation reactions, which are also known as Henkel reactions. Van Haveren et al. describe a method to produce a mixture of furan-2,5-dicarboxylate and furan-2,4-dicarboxylate by heating furan-2-carboxylate salts in the presence of a Cd, Zn, or Fe-based catalyst in U.S. Pat. No. 9,284,290, which is incorporated by reference for all purposes. Similarly, Brownscombe et al. describe the use of Henkel reactions to convert arene monocarboxylates into arene dicarboxylates by heating arene monocarboxylate salts with a disproportionation catalyst in U.S. Pat. Nos. 6,479,699 and 6,452,045, which are incorporated by reference for all purposes. These methods are not useful for the synthesis of furan-2,5-dicarboxylate because i) disproportionation reactions are limited to a maximum yield of 50%, in contrast to $CO_3^{2-}$-promoted C—H carboxylation, which has a maximum yield of 100%; ii) the use of the catalyst complicates process chemistry by necessitating removal and recycling of the catalyst; iii) the catalyst is commonly based on Cd, which is highly toxic; iv) the formation of multiple furan dicarboxylate isomers creates a major purification challenge.

This specification shows that $CO_3^{2-}$-promoted C—H carboxylation of furan-2-carboxylate proceeds efficiently under solvent- and catalyst-free conditions in partially molten salt mixtures containing alkali cations (e.g. $Cs^+$ or $K^+$) at intermediate temperatures. In these reaction media, ($CO_3^{2-}$) can deprotonate the very weakly acidic C—H bond of furan-2-carboxylate, generating a carbon-centered nucleophile that reacts with $CO_2$ to form furan-2,5-dicarboxylate.

Carbonate-promoted C—H carboxylation of furan-2-carboxylate proceeds at elevated temperature and does not require a catalyst or solvent. Conditions have been previously described that produce high yields of the desired furan-2,5-dicarboxylate product in Banerjee et al. *Nature* 531 215-219 (2016) and Dick et al. *Green Chem.* 19, 2966-2972 (2017) which are incorporated by reference for all purposes, but the reaction times are impractical for high-volume production or commercial applications. Various embodiments in this specification reduce the reaction time required to achieve high yields for carbonate-promoted C—H carboxylation of furan-2-carboxylate.

The description of the features that lead to a reduction in the reaction time is better understood by first describing the phase properties for one embodiment of the C—H carboxylation reaction, which is described in detail in Frankhouser, A. D., Kanan M. W. "Phase behavior that enables solvent-free carbonate-promoted furoate carboxylation" *J. Chem. Phys. Lett.* 11, 7544-7551 (2020), which is incorporated by reference for all purposes. The carboxylation of furan-2-carboxylate to form furan-2,5-dicarboxylate proceeds according to the following equation:

$$MFA + 1/2\ M_2CO_3 + 1/2\ CO_2 \rightarrow M_2FDCA + 1/2\ H_2O$$

where MFA denotes a salt comprised of $M^+$ and $FA^-$, where $M^+$ denotes an alkali cation or mixture of alkali cations and $FA^-$ is the furan-2-carboxylate anion, $M_2CO_3$ denotes a salt comprised of $M^+$ and $CO_3^{2-}$, which is the carbonate anion, and $M_2FDCA$ denotes a salt comprised of $M^+$ and $FDCA^{2-}$, where $FDCA^{2-}$ denotes the furan-2,5-dicarboxylate anion. The reaction can be carried out with excess $M_2CO_3$, but the stoichiometric relation above defines the minimum amount required for full conversion (i.e. $M_2CO_3$:MFA≥0.5 in terms of molar equivalents). The $CO_2$ may be provided as a static pressure or flowing gas. When a flow of $CO_2$ is provided, the $H_2O$ produced as a byproduct is stripped from the system. In some embodiments, only one alkali cation ($M^+$) is used. In other embodiments, more than one alkali cation may be used. In other embodiments, additional components may be added, including additional salts such as alkali salts of other carboxylates (e.g. alkali formate or alkali acetate), or other salts containing non-alkali cations, including divalent and trivalent cations. Additional gases may also be provided along with $CO_2$.

Figure 1A:
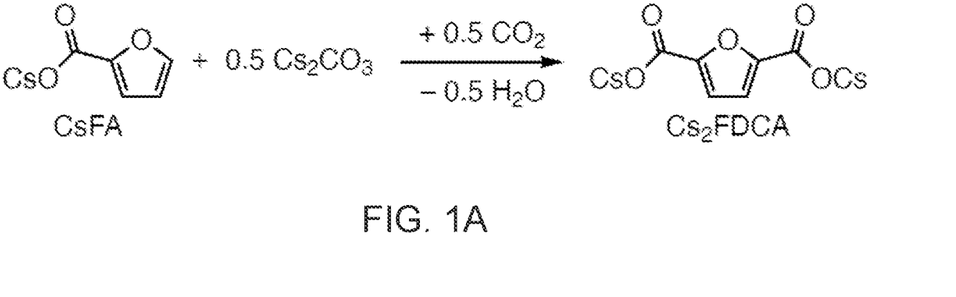
FIG. 1A is a chemical equation showing the reaction of cesium furan-2-carboxylate, cesium carbonate, and $CO_2$ to form cesium furan-2,5-dicarboxylate.
Figure 1B:
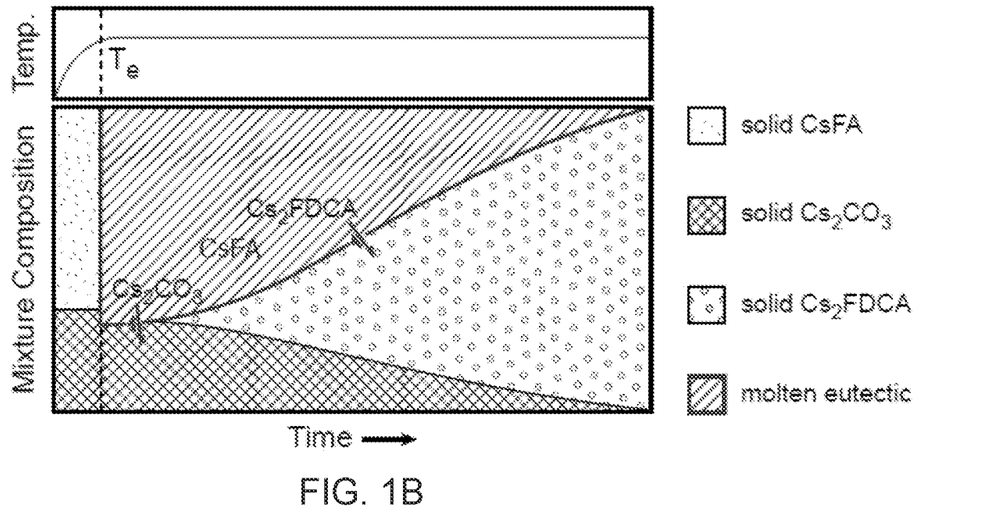
FIG. 1B is a schematic depiction of the phase composition of the reaction in FIG. 1A as a function of conversion.

In a preferred embodiment, $M^+$ is $Cs^+$ and no additional salts are used. FIG. 1A shows the equation for the carboxylation of cesium furan-2-carboxylate with $Cs_2CO_3$ and $CO_2$ with the chemical structures drawn. FIG. 1B shows a schematic depiction of the evolution of the phase composition of this reaction as a function of conversion. The phase behavior is further described below. Both salts in the starting material (CsFA and $Cs_2CO_3$) are solid at room temperature, and the reaction will not proceed from this state. Heating a mixture of these two salts above its eutectic temperature ($T_e$) at 256° C. results in the formation of a molten eutectic that consists of CsFA and a minor amount of $Cs_2CO_3$. (The eutectic temperature of 256° C. for the CsFA/$Cs_2CO_3$ system is measured by differential scanning calorimetry, which carefully controls and accurately measures the sample temperature.) Most of the $Cs_2CO_3$ remains in its solid state at this initial stage. The reaction mixture thus initially consists of three phases: molten eutectic (CsFA and $Cs_2CO_3$), solid ($Cs_2CO_3$), and gas ($CO_2$). Once eutectic melting occurs, exposure of the mixture to $CO_2$ gas will result in the formation of $Cs_2FDCA$ product according to the reaction shown above. The reaction results in the consumption of $Cs_2CO_3$ and CsFA. As $Cs_2CO_3$ in the melt is consumed, it remains in equilibrium with the solid $Cs_2CO_3$ phase. In this way, $Cs_2FDCA$ production also results in the consumption of the solid $Cs_2CO_3$ phase. At low conversion, the $Cs_2FDCA$ produced remains fully dissolved in the molten phase, such that the mixture continues to consist of three phases: molten eutectic (CsFA, $Cs_2CO_3$, and $Cs_2FDCA$), solid ($Cs_2CO_3$), and gas ($CO_2$ and $H_2O$). At conversions higher than ~5%, $Cs_2FDCA$ saturates the melt. Any additional $Cs_2FDCA$ produced after this point will precipitate as an additional solid phase. Thus, for the remainder of the reaction, the mixture consists of four phases: molten eutectic (CsFA, $Cs_2CO_3$, and $Cs_2FDCA$), solid $Cs_2CO_3$, solid $Cs_2FDCA$, and gas ($CO_2$ and $H_2O$). Both solid components remain in equilibrium with their constituent components in the molten phase. Increasing conversion results in the diminution of the molten phase and solid $Cs_2CO_3$, with the accumulation of solid $Cs_2FDCA$.

As the reaction progresses, the solid $Cs_2FDCA$ phase will make up an increasingly large fraction of the mixture. Without some form of agitation, domains of solid $Cs_2FDCA$ will continuously increase in size, eventually encasing the diminishing molten domains and limiting mass transport in two key ways. Firstly, decreased contact between the molten domains and solid $Cs_2CO_3$ limits the transport of $Cs_2CO_3$ into the molten phase. Secondly, transport of $CO_2$ gas into the molten phase (and, conversely, transport of $H_2O$ out) is inhibited.

Practically, and depending on process specifics such as temperature and reactor design, these mass transport limitations can lead to i) slow reaction kinetics (i.e. "stalling" of the reaction at low conversion, long reaction times), or ii) increased decomposition (i.e. decreased yield of the desired product due to starting materials reacting through undesired pathways in the absence of the reaction component(s) necessary for the desired pathway to produce $FDCA^{2-}$).

In various embodiments, agitation of the reaction mixture can be used to avoid the situation described above and achieve high-yielding carboxylation reactions in short time periods if the agitation serves to break up the solid product. Solid $Cs_2FDCA$ will still accumulate as the reaction proceeds, but agitation that breaks up the solid $Cs_2FDCA$ domains can ensure adequate contact between the molten phase where the reaction occurs and the solid and gas-phase reactants necessary for the reaction to proceed. The mode of agitation must be able to i) maintain a high degree of contact between the solid, molten, and gas-phase components of the reaction mixture, and ii) maintain this contact for a reaction mixture whose phase composition changes over time (i.e. becomes more solid and less molten as a function of conversion).

Because the properties of a eutectic mixture are specific to its components, changes to the composition of the starting material for this reaction will impact its phase behavior and thus influence both whether the reaction can proceed and, if so, under what conditions. Use of $M^+$ other than $Cs^+$ impacts the phase behavior of the salt mixture. When a single alkali cation is used, only the $Cs^+$ salts provide a viable temperature operating window where a molten phase can be accessed without rapid decomposition of the furan-2-carboxylate. However, eutectic melting (and hence carboxylation) can be observed for furoate/carbonate mixtures with multiple alkali cations, as long as at least a small amount of cesium salts are present.

Additional components can be added to the mixture to modify its phase behavior. Ideally, these components would create a larger temperature operating window by inducing eutectic melting of furoate/carbonate at a lower temperature, while themselves remaining inert and thermally stable under the reaction conditions. As an example, potassium isobutyrate salt can be added to a mixture of potassium furoate and carbonate (i.e. KFA and $K_2CO_3$) to induce eutectic melting and enable carboxylation reactivity, whereas the $KFA/K_2CO_3$ mixture in the absence of isobutyrate does not exhibit eutectic melting and is hence unreactive.

Due to the effects that these compositional changes will have on the phase behavior of the mixture, process specifics such as temperature and residence time would need to be optimized for a given mixture composition. However, the general observations made in the embodiment starting with only CsFA and $Cs_2CO_3$ (e.g. presence of both solid and molten components, changing phase composition of the mixture as a function of conversion) will still apply, meaning that the process insights are not limited to one specific composition.

It is important to note that the temperatures of phase transitions measured by thermal analytical techniques such as differential scanning calorimetry correspond to the sample temperature, which is carefully controlled and accurately measured in these analytical techniques. However, the temperature measured for a reaction depends on the placement of the thermocouple or thermometer within or external to the reactor and the thermal gradients that form under the reaction conditions, which can be substantial. Thus, the temperature of a reaction, as measured by a thermocouple or thermometer applied to the reactor, may appear to be below or above the temperature required to achieve partial melting of the reaction mixture as measured by thermal analytical techniques if there is a gradient between the reaction mixture and the thermocouple or thermometer.

Figure 2:
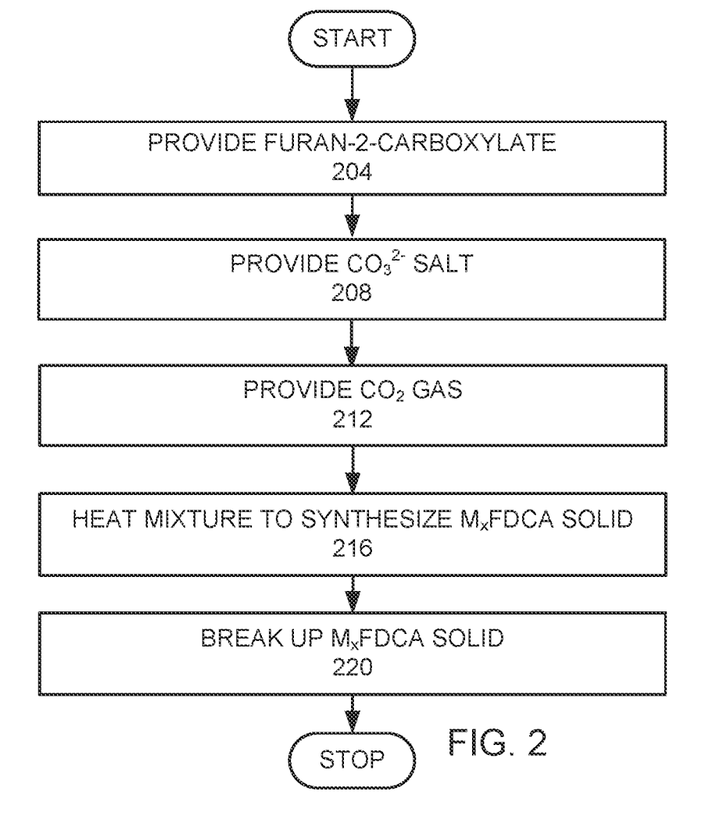
FIG. 2 is a high level flow chart of an embodiment.

In order to facilitate understanding, FIG. 2 is a high level flow chart of an embodiment. Various embodiments may have more or less steps and may perform steps in a different order or simultaneously. A salt comprising furan-2-carboxylate with cation $M^+$ and/or $M^{2+}$ is provided (step 204). The salt comprising furan-2-carboxylate may be provided as a solution and/or a solid. A salt comprising $CO_3^{2-}$ with cation $M^+$ or $M^{2+}$ is provided (step 208). The salt comprising $CO_3^{2-}$ may be provided as a solution or a solid. The salt comprising furan-2-carboxylate and the salt comprising $CO_3^{2-}$ form a mixture. In some embodiments, the salt comprising $CO_3^{2-}$ may be provided before or simultaneously with providing the salt comprising furan-2-carboxylate. If the salt comprising furan-2-carboxylate and/or the salt comprising $CO_3^{2-}$ is provided as a solution, the solvent is removed to form a solid. A solution of furan-2-carboxylate may be mixed with a solution of $CO_3^{2-}$ and then the solvent is removed to form the mixture. A $CO_2$ gas is provided to the mixture (step 212). The $CO_2$ gas may be provided by exposing the mixture to the $CO_2$ gas under pressure. The mixture is heated to a temperature to at least partially melt the mixture, wherein the heating of the mixture causes the synthesizing of a $M_xFDCA$ solid (step 216), wherein $M_xFDCA$ denotes a salt comprising furan-2,5-dicarboxylate ($FDCA^{2-}$) and cation $M^+$ and/or $M^{2+}$, where x is a number between 1 and 2, inclusive. The mixture containing furan-2-carboxylate is mechanically agitated, wherein the mechanical agitating breaks up the $M_xFDCA$ solid.

The reaction and mixture used for the synthesizing of $M_xFDCA$ are substantially free from catalysts. Specifically, the reaction is substantially free from metal-based catalysts. More specifically, the reaction is substantially free from metal based catalysts commonly used for Henkel reactions (disproportionations) including zinc compounds, cadmium compounds, mercury compounds, and iron compounds in the form of, for example, halides, oxides, carbonates, carboxylates, or sulfates of these metals. An advantage of having a reaction using a mixture that is substantially free of such catalysts is that the resulting material does not need to be further processed to recycle and/or remove the catalyst. Since many catalysts contain toxic metals, another advantage of having a reaction that is substantially free of catalysts is that the product is not contaminated with toxic metals. In addition, various embodiments provide higher yields without needing a catalyst. Various embodiments provide a process and/or reaction that is substantially metal free so that the product is substantially metal free.

The need to apply mechanical agitation that can break up the solid $M_xFDCA$ product in order to improve the reaction rate while maintaining a high yield of the product is an unexpected feature of the carboxylation of furan-2-carboxylate that arises from its unusual phase behavior that is schematically summarized in FIG. 1B. Reactions involving solid phase reactants and gas phase reactants are commonly performed in fluidized bed reactors where the solid reactant (s) are fluidized in the gaseous reactant(s), as described in Werther, Joachim. "Fluidized Bed Reactors" in *Ullmann's Encyclopedia of Industrial Chemistry* (2000), which is incorporated by reference for all purposes. By contrast, the carboxylation of furan-2-carboxylate proceeds in a molten phase that prevents fluidization of the non-gaseous reactants because molten components cause particles to agglomerate. Reactions that proceed in a molten phase can often be performed without agitation or with simple stirring because there is sufficient mass transport in the molten medium, which is typically at elevated temperature. By contrast, simple stirring is insufficient to enable a high reaction rate in the carboxylation of furan-2-carboxylate because the proportion of molten phase diminishes as the conversion increases and the accumulation of solid $M_xFDCA$ product imposes a barrier between the reactants in the molten phase and the gaseous $CO_2$. It was unexpectedly found through experimentation that by breaking up solid $M_xFDCA$ product, the carboxylation reaction produces more than 80% yield of the furan-2,5-dicarboxylate product in less than an hour. Such a high yield at such a low reaction time was unexpected. Such a process increases throughput and reduces costs in time and energy.

EXAMPLES

Example 1

Figure 3A:
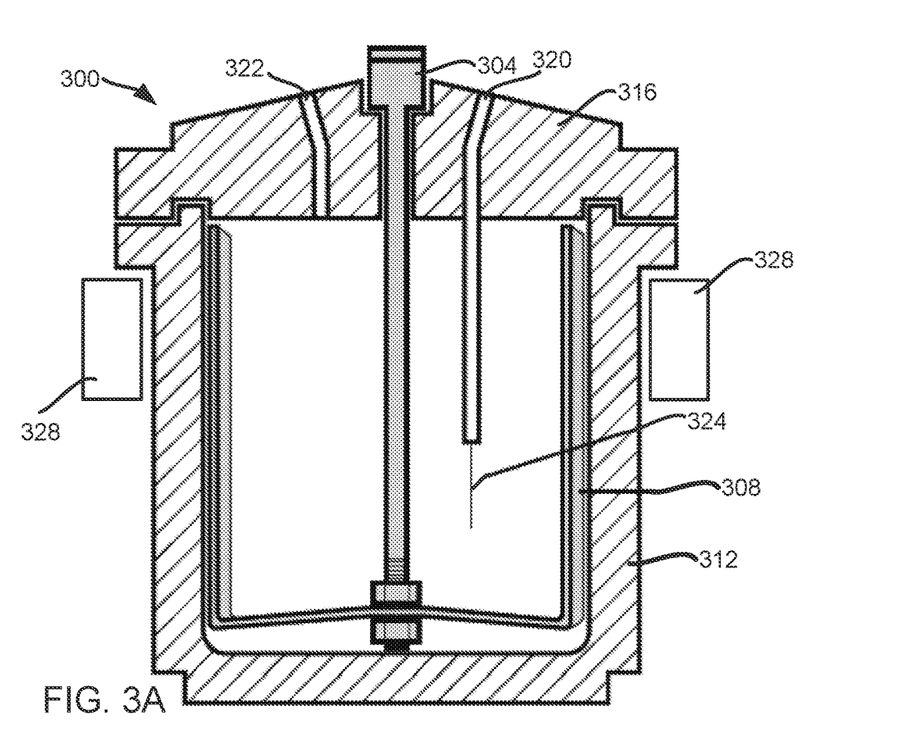
FIG. 3A is a schematic of a reactor used to perform C—H carboxylation of furan-2-carboxylate.
Figure 3B:
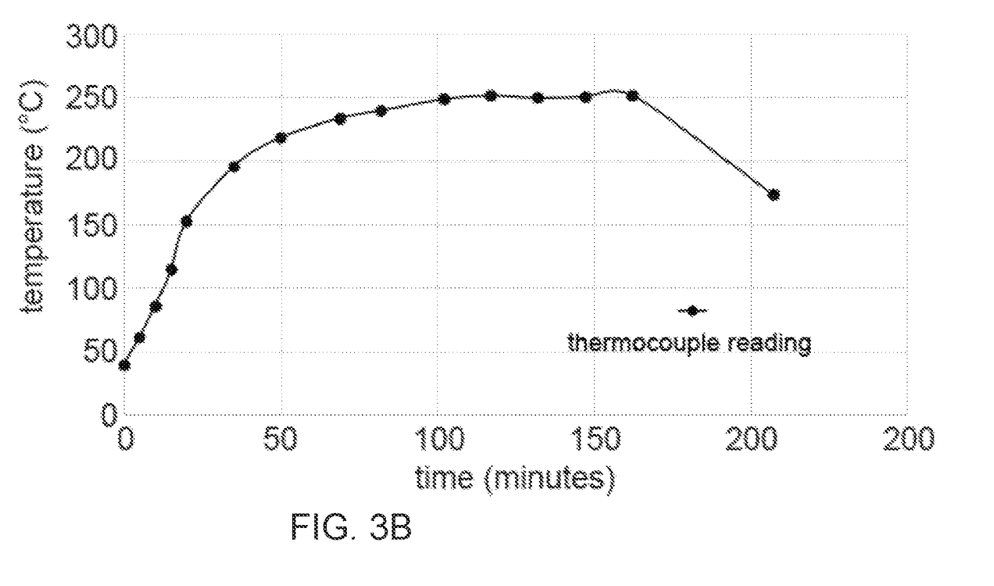
FIG. 3B is the temperature profile of the thermocouple for the reaction described in EXAMPLE 1.
Figure 3C:
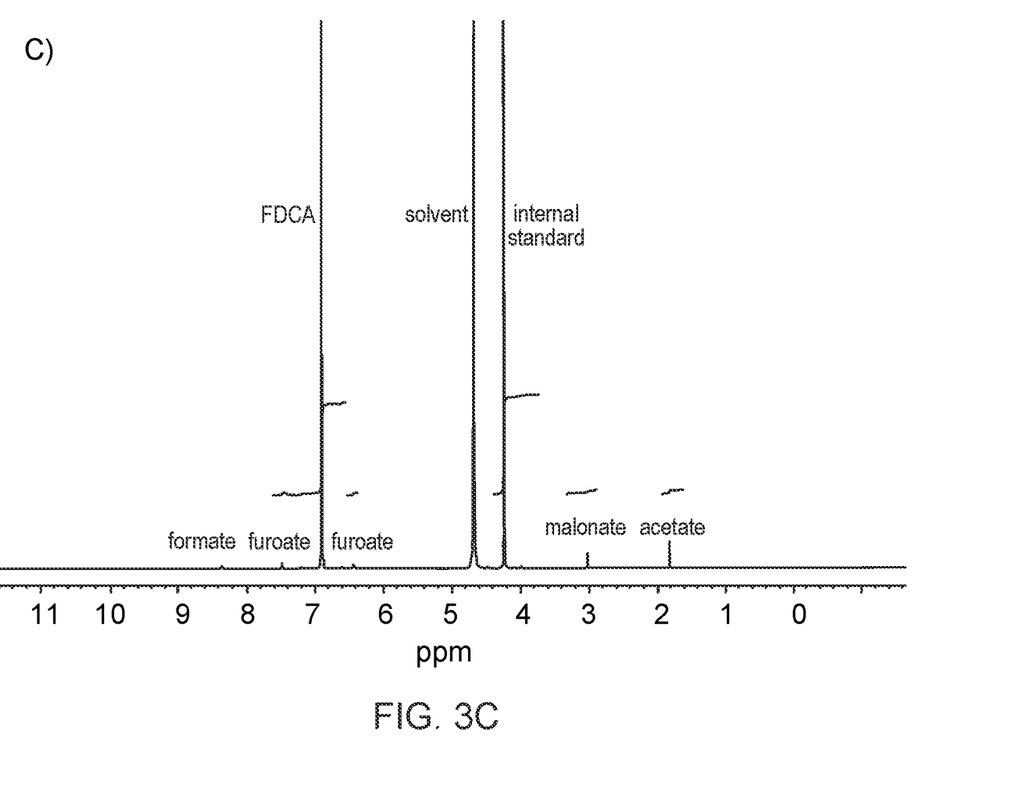
FIG. 3C is the crude $^1H$ NMR of the product of the reaction in EXAMPLE 1.

In a specific example of an embodiment where an experiment was carried out, a salt mixture composed of cesium furan-2-carboxylate (CsFA) and 0.55 equivalents of cesium carbonate ($Cs_2CO_3$) was prepared by combing furan-2-carboxylic acid and 1.05 equivalents of $Cs_2CO_3$ in water and evaporating to dryness on a hotplate at 150° C. The resulting salt was dried overnight at 150° C. in a vacuum oven and stored in a sealed container until use. FIG. 3A is a schematic view of a reactor 300 that may be used in an embodiment. In this embodiment, the reactor 300 is a Parr reactor equipped with an anchor stirrer 304 attached to a wall scraper 308. The wall scraper 308 is adjacent to chamber walls 312 of the reactor 300. In this embodiment, the anchor stirrer 304 passes through a reactor cover 316. In this embodiment, inlet ports 320 and outlet ports 322 are formed in the reactor cover 316 to provide the $CO_2$ gas. A thermocouple 324 is placed inside the reactor 300. 100 g of a salt mixture composed of CsFA and 0.55 equivalents of $Cs_2CO_3$ is placed in the reactor 300 and the reactor was purged with $CO_2$. In this example, a heater 328 heated the reactor until the thermocouple reached a temperature of 252° C., while $CO_2$ was simultaneously flowed at 5.5 standard liters per minute (slpm) at 275 psig and the anchor stirrer 304 equipped with the wall scraper 308 was rotated at 150 rpm. The line providing $CO_2$ to the reactor was heated to 350° C. to ensure that the gas flow did not cool the reaction mixture. After 60 min with the thermocouple at 252° C., the heater 328 was turned off. The temperature profile of the thermocouple is shown in FIG. 3B. After cooling, the reactor was opened and solid contents were removed by dissolving in $H_2O$. An aliquot of the solution was dried and analyzed by $^1H$ NMR ($D_2O$) with an internal standard indicated 82.4 g of cesium furan-2,5-dicarboxylate ($Cs_2FDCA$) (83% yield) and 5.1 g remaining CsFA (5%) (FIG. 3C). The mass balance was comprised of carbonaceous decomposition products.

Example 2

A reaction was performed under the same conditions as EXAMPLE 1 except that 200 g of the starting salt mixture was used instead of 100 g. Quantitative $^1H$ NMR analysis of the products indicated 158.8 g $Cs_2FDCA$ (80% yield) and 18 g of remaining CsFA (9%).

Example 3

A reaction was performed under the same conditions as EXAMPLE 1 except that the reactor was maintained at a temperature where the thermocouple read 251° C. for 40 min instead of 60 min. Quantitative $^1H$ NMR analysis of the products indicated 77.5 g $Cs_2FDCA$ (78% yield) and 11.8 g of remaining CsFA (12%).

In the specification and claims, a carboxylate salt is a salt comprised of an anion that is an organic compound with a deprotonated carboxylic acid (also referred to as carboxylate) and a cation that is an alkali cation, alkaline earth cation, or other metal cation.

Embodiments of Implementation

It will be obvious to those with skill in the art that instead of providing a salt comprising $CO_3^{2-}$, inorganic base salts, such as a salt comprising hydroxide ($OH^-$) or oxide ($O^{2-}$) could be provided, which would upon exposure to $CO_2$ react with the $CO_2$ to form a salt comprising substantially $CO_3^{2-}$. In addition, conditions under which $CO_3^{2-}$ promotes a carboxylation reaction will also enable the use of other inorganic bases other than $CO_3^{2-}$, such as phosphate ($PO_4^{3-}$) or borate ($B(OH)_4^-$), provided as salts with alkali, alkaline earth, or other cations. In general, the use of $CO_3^{2-}$ is preferred because $CO_3^{2-}$ salts tend to be less expensive and corrosive than other bases and because $CO_3^{2-}$ salts are consumed in the carboxylation reaction, forming water as the only byproduct.

In the specification and claims when comparing amounts of elements or ions or molecules, unless otherwise specified, the number of moles of the element or ion or molecule is being compared.

In various embodiments, a method for synthesizing furan-2, 5-dicarboxylate ($FDCA^{2-}$) is provided. Furan-2-carboxylate is provided. In some embodiments, furan-2-carboxylate is provided as a salt comprising furan-2-carboxylate. In other embodiments, furan-2-carboxylic acid is combined with a salt comprising $CO_3^{2-}$ or another base such as $OH^-$ to form a mixture, which converts the furan-2-carboxylic acid to a salt comprising furan-2-carboxylate. The salt comprising furan-2-carboxylate is combined with a salt comprising $CO_3^{2-}$ to form a mixture. The mixture is heated to a temperature to at least partially melt the mixture, wherein the heating of the mixture causes the synthesizing of a salt comprising furan-2, 5-dicarboxylate ($FDCA^{2-}$). The salt comprising $FDCA^{2-}$ is herein referred to as an $FDCA^{2-}$ salt. In some embodiments, the $FDCA^{2-}$ salt is $M_2FDCA$, wherein $M^+$ is a monovalent cation. In other embodiments, the $FDCA^{2-}$ salt is MFDCA, wherein $M^{2+}$ is a divalent cation. In other embodiments, the $FDCA^{2-}$ salt contains a mixture of $M^+$ and $M^{2+}$ cations. During the reaction, a solid comprising $FDCA^{2-}$ salt is formed. The reaction mixture containing furan-2-carboxylate is mechanically agitated, wherein the mechanical agitation serves to break up the solid comprising $FDCA^{2-}$ salt. In some embodiments, the furan-2-carboxylate is provided as part of a salt with $M^+$ cations.

The $CO_3^{2-}$ salt is also provided with $M^+$ cations. In some embodiments, the $M^+$ cations are alkali cations. In some embodiments, the $M^+$ cations are either $Cs^+$ or $K^+$.

In various embodiments, the mechanical agitation of the mixture sufficient to break up the solid comprising $FDCA^{2-}$ salt may be provided by various apparatus. For example, mechanical agitation is provided by an agitator, such as an impeller, one or more screws, a scraper, or a ball mill. For mechanical agitation by an impellor, the torque applied to the impeller must be sufficient to break the solid comprising $FDCA^{2-}$ salt, given the geometry of the blades of the impeller and the speed of rotation. For mechanical agitation by screws, the reaction may be performed continuously in an extruder, wherein the screws are used to push the reaction mixture through the reactor and continuously break up the solid components. In some embodiments, mechanical agitation is provided by sound waves, such as ultrasound, with sufficient energy to break the solid comprising $FDCA^{2-}$ salt.

Figure 4:
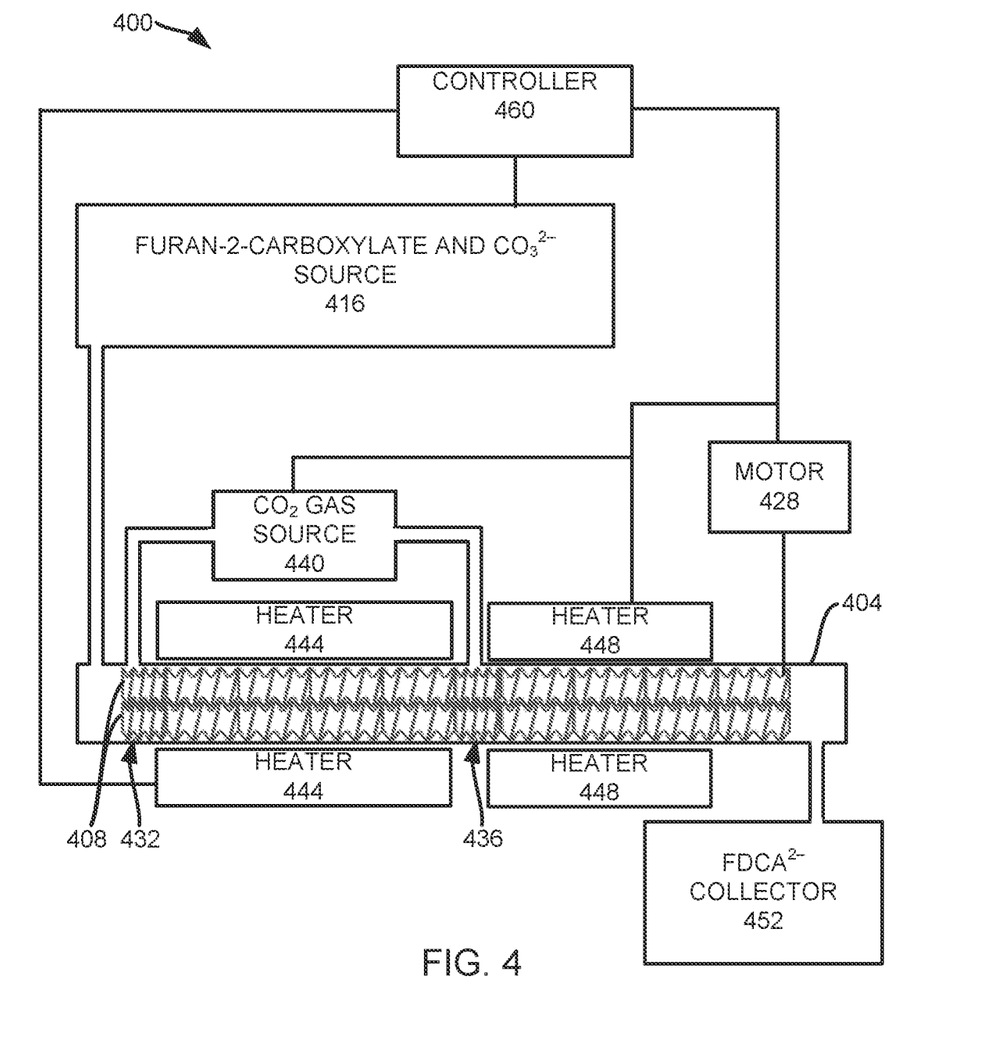
FIG. 4 is a schematic view of another reactor that may be used in another embodiment.

FIG. 4 is a schematic view of a reactor 400 that may be used in another embodiment. In this embodiment a reactor chamber 404 houses two screws 408. In this embodiment, the furan-2-carboxylate and $CO_3^{2-}$ salt are provided from a single source 416. The use of a single source 416 allows for the furan-2-carboxylate and $CO_3^{2-}$ salt to be thoroughly mixed at the proper ratio before being added to the reactor chamber 404. The thorough mixing at the proper ratio may be performed by mixing an aqueous solution of furan-2-carboxylate with an aqueous solution of $CO_3^{2-}$ salt at the proper ratios and then drying the resulting solution to provide a solid. A motor 428 drives the two screws 408 so that the two screws 408 draw the mixture from the input side of the reactor chamber 404 through the reactor chamber 404 to an output side of the reactor chamber 404. In this embodiment, the two screws 408 have a first region 432 and a second region 436 where the threads of the two screws 408 have a tighter pitch causing the mixture to move more slowly through the first region 432 and the second region 436. In this embodiment, at the first region 432 and the second region 436, $CO_2$ gas is provided from a $CO_2$ gas source 440. A first heater 444 is provided to heat a first part of the reactor chamber 404. A second heater 448 is provided to heat a second part of the reactor chamber 404. The two screws 408 move the mixture from the input side of the reactor chamber 404 through the first region 432, where $CO_2$ gas is provided, past the first heater 444 where the mixture is heated to provide molten mixture and a $M_xFDCA$ solid is synthesized, then past the second region 436, where more $CO_2$ gas is provided, then past the second heater 448 that provides a lower temperature than the first heater 444, so that when the mixture is provided to the output side of the reactor chamber 404 the molten mixture has solidified. Solid furan-2, 5-dicarboxylate is then provided to a collector 452. In this embodiment, the furan-2-carboxylate and $CO_3^{2-}$ salt can be continuously added to the reactor chamber 404 with $CO_2$ gas, while the furan-2, 5-dicarboxylate is continuously extracted.

A controller 460 may be connected to the furan-2-carboxylate and $CO_3^{2-}$ source 416, the motor 428, the $CO_2$ gas source, the first heater 444, and the second heater 448. The controller 460 may have computer readable media with computer readable code for providing the mixture of furan-2-carboxylate and $CO_3^{2-}$ salt, driving the two screws 408, providing the $CO_2$ gas, and heating the reactor chamber 404 with the first heater 444 and the second heater 448. The controller 460 may allow the continuous processing. The controller 460 may have computer readable code to provide the right pressure of $CO_2$, the right temperatures of the first heater 444 and the second heater 448, and the right speed of the two screws 408.

In various embodiments, the range of ratios for $CO_3^{2-}$ to furan-2-carboxylate (i.e. moles $CO_3^{2-}$ to moles furan-2-carboxylate) is from 1:4 to 2:1, inclusive. All of the provided ranges are inclusive. More preferably, the range of ratios for $CO_3^{2-}$ to furan-2-carboxylate is from 1:2 to 1:1, inclusive. In some embodiments, the range of $CO_2$ pressures is from 0.1 bar to 60 bar. In other embodiments, the range of $CO_2$ pressures is 1 bar to 60 bar. In other embodiments, the range of $CO_2$ pressures is 5 bar to 60 bar. In some embodiments, the temperature is in the range of 150° C. to 450° C. In other embodiments, the temperature is in the range of 200° C. to 350° C. In other embodiments, the temperature is in the range of 225° C. to 300° C.

Figure 5:
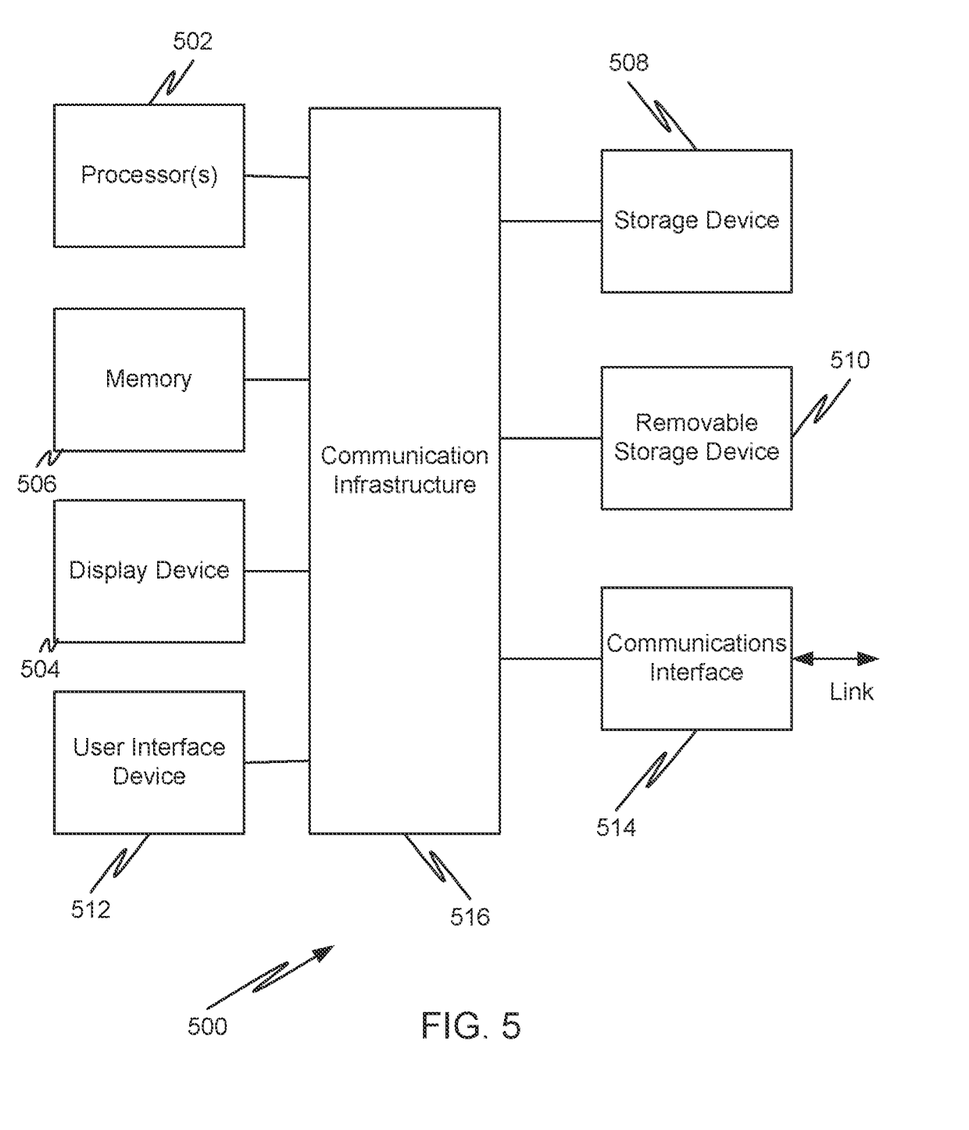
FIG. 5 is a high-level block diagram showing a computer system, which may be used to provide a controller.

FIG. 5 is a high-level block diagram showing a computer system 500, which may be used to provide the controller 460. The computer system may have many physical forms ranging from an integrated circuit, a printed circuit board, and a small handheld device up to a computer. The computer system 500 includes one or more processors 502, and further can include an electronic display device 504, a main memory 506 (e.g., random access memory (RAM)), data storage device 508 (e.g., hard disk drive), removable storage device 510 (e.g., optical disk drive), user interface devices 512 (e.g., keyboards, touch screens, keypads, mice or other pointing devices, etc.), and a communication interface 514 (e.g., wireless network interface). The communication interface 514 allows software and data to be transferred between the computer system 500 and external devices via a link. The system may also include a communications infrastructure 516 (e.g., a communications bus, cross-over bar, or network) to which the aforementioned devices/modules are connected.

Information transferred via communications interface 514 may be in the form of signals such as electronic, electromagnetic, optical, or other signals capable of being received by communications interface 514, via a communication link that carries signals and may be implemented using wire, cable, fiber optics, a phone line, a cellular phone link, a radio frequency link, and/or other communication channels. With such a communications interface, it is contemplated that the one or more processors 502 might receive information from a network, or might output information to the network in the course of performing the above-described method steps. Furthermore, method embodiments of the present invention may execute solely upon the processors or may execute over a network such as the Internet in conjunction with remote processors that share a portion of the processing.

The term "non-transient computer readable media" is used generally to refer to media such as main memory, secondary memory, removable storage, and storage devices, such as hard disks, flash memory, disk drive memory, CD-ROM, and other forms of persistent memory and shall not be construed to cover transitory subject matter, such as carrier waves or signals. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

In other embodiments, instead of providing mechanical agitation to break up the solid comprising $FDCA^{2-}$ salt while the mixture is partially molten, the mixture is cooled and formed into a solid. Then mechanical agitation is provided to break up particle sizes of the solid mixture. The mixture is then heated to at least partially melt the mixture. The heating, then cooling, and then mechanical agitation may be repeated for several cycles.

While this invention has been described in terms of several preferred embodiments, there are alterations, permutations, modifications, and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for synthesizing furan-2, 5-dicarboxylate ($FDCA^{2-}$), comprising:
    providing furan-2-carboxylate;
    providing an inorganic base in a form of an inorganic base salt, wherein the furan-2-carboxylate and the inorganic base salt form a mixture;
    providing a $CO_2$ gas to the mixture;
    heating the mixture to a temperature to at least partially melt the mixture, wherein the heating of the mixture causes the synthesizing of a $M_xFDCA$ solid, wherein $M_xFDCA$ denotes a salt comprising furan-2,5-dicarboxylate ($FDCA^{2-}$) and cation $M^+$ or $M^{2+}$, where x is a number between 1 and 2, inclusive; and
    mechanically agitating the mixture containing furan-2-carboxylate, wherein the mechanically agitating breaks up the $M_xFDCA$ solid.

2. The method, as recited in claim 1, wherein the inorganic base salt is a $CO_3^{2-}$ salt.

3. The method, as recited in claim 2, wherein cation $M^+$ is an alkali cation and cation $M^{2+}$ is an alkaline earth cation.

4. The method, as recited in claim 2, wherein $M^+$ is a $Cs^+$ cation.

5. The method, as recited in claim 1 wherein the mechanically agitating is performed using an impellor, wherein a speed of rotation of the impellor and geometry of the impellor allow the impeller to break up the $M_xFDCA$ solid.

6. The method, as recited in claim 1 wherein the mechanically agitating is performed in an extruder using one or more screws to break up the $M_xFDCA$ solid.

7. The method, as recited in claim 1 wherein the mechanically agitating is performed in a ball mill.

8. The method, as recited in claim 1 wherein $CO_2$ is flowed through a reactor for agitating the mixture.

9. The method, as recited in claim 1, wherein the mixture is substantially catalyst free.

10. The method, as recited in claim 1, wherein the mixture is substantially free of zinc compounds, cadmium compounds, mercury compounds, and iron compounds.

11. The method, as recited in claim 1, wherein heating the mixture is substantially free of metal containing catalyst.

12. The method, as recited in claim 1, wherein the inorganic base salt and $CO_2$ gas form a $CO_3^{2-}$ salt.

13. The method, as recited in claim 1, wherein the providing furan-2-carboxylate provides furan-2-carboxylate in a solution and wherein the providing the inorganic base provides the inorganic base in a solution, wherein the mixture is a solution with a solvent, further comprising removing the solvent of the solution.

14. A method for synthesizing furan-2, 5-dicarboxylate ($FDCA^{2-}$), comprising:
    providing furan-2-carboxylate;
    providing an inorganic base in a form of an inorganic base salt, wherein the furan-2-carboxylate and the inorganic base salt form a mixture;
    providing a $CO_2$ gas to the mixture;
    heating the mixture to a temperature to at least partially melt the mixture, wherein the heating of the mixture causes the synthesizing of a $M_xFDCA$ solid, wherein $M_xFDCA$ denotes a salt comprising furan-2,5-dicarboxylate ($FDCA^{2-}$) and cation $M^+$ or $M^{2+}$, where x is a number between 1 and 2, inclusive; and
    cooling the mixture to solidify the mixture to form a solid mixture;
    reducing particle sizes of the solid mixture; and
    reheating the mixture while providing a $CO_2$ gas to partially melt the mixture.

15. The method as cited in claim 14, wherein the cooling the mixture to solidify the mixture reduces sizes of the solid mixture.

16. The method, as recited in claim 14, wherein the inorganic base salt is a $CO_3^{2-}$ salt.

17. The method, as recited in claim 14, wherein $M^+$ is an alkali cation or mixture of alkali cations.

18. The method, as recited in claim 14, wherein $M^+$ is a $Cs^+$ cation.

19. The method, as recited in claim 14, wherein the heating of the mixture is substantially catalyst free.

20. The method, as recited in claim 14, wherein the heating of the mixture is substantially free of zinc compounds, cadmium compounds, mercury compounds, and iron compounds.

* * * * *